United States Patent
Mueller et al.

[11] Patent Number: 5,869,804
[45] Date of Patent: Feb. 9, 1999

[54] LASER-WELDED BALL-AND-SOCKET CONNECTION

[75] Inventors: David E. Mueller, Santa Clarita; Stephen M. Jones, Canyon County; Arthur A. Campbell, Stevenson Ranch; Jerlye L. Walter, Newhall, all of Calif.

[73] Assignee: Pacesetter, Inc., Sylmar, Calif.

[21] Appl. No.: 670,861

[22] Filed: Jun. 28, 1996

[51] Int. Cl.$^6$ .................................................. B23K 26/00
[52] U.S. Cl. ........................................ 219/121.64; 607/37
[58] Field of Search ........................ 219/121.63, 121.64, 219/121.13, 121.14; 228/6.2, 44.7; 607/37, 116, 122, 123, 125, 126, 127, 128; 174/84 R

[56] References Cited

U.S. PATENT DOCUMENTS

| | | | |
|---|---|---|---|
| 4,711,027 | 12/1987 | Harris ..................................... | 174/84 R |
| 5,067,903 | 11/1991 | Szyszkowski ............................. | 439/55 |
| 5,103,818 | 4/1992 | Maston et al. ......................... | 128/419 P |
| 5,235,742 | 8/1993 | Szyszkowski ............................. | 29/856 |
| 5,282,841 | 2/1994 | Szyszkowski ............................. | 607/36 |
| 5,458,629 | 10/1995 | Baudino et al. ........................ | 607/116 |
| 5,569,883 | 10/1996 | Walter et al. .......................... | 174/84 R |

FOREIGN PATENT DOCUMENTS

| | | | |
|---|---|---|---|
| 58-90389 | 5/1983 | Japan ................................ | 219/121.64 |
| 4-242705 | 8/1992 | Japan . | |

Primary Examiner—Geoffrey S. Evans

[57] ABSTRACT

A method is presented of welding an electrically conductive termination component having first and second opposed surfaces to an electrically conductive elongate member extending to a terminal end. The method comprises the steps of forming a substantially circular aperture through the termination component and defined by a rim having a diameter substantially equivalent to the transverse dimension of the elongate member. The terminal end of the elongate member is positioned proximate the termination component overlying the rim of the aperture such that the longitudinal axis of the elongate member is generally coplanar with the center of the aperture. Then, a laser beam is directed transversely of the termination component through the aperture therein toward and onto the elongate member to simultaneously melt the elongate member and the termination component in the region of the aperture and create a mixture of the molten material of both the elongate member and the termination component within the aperture. Upon the cessation of operation of the laser beam, the mixture of the molten material solidifies within the aperture and between the termination component and the elongate member to thereby achieve a welded connection between the elongate member and the termination component. In a preferred embodiment, a ball member is formed at an end of the elongate member and the rim of the aperture in the termination component has a diameter smaller than that of the ball member and the ball member is positioned in engagement with the rim of the aperture.

20 Claims, 5 Drawing Sheets

LASER-WELDED BALL-AND-SOCKET CONNECTION

FIELD OF THE INVENTION

This invention relates generally to improvements in a technique for laser welding small size wire including coiled wire and connectors. In one application, which is not intended to be restrictive of the invention, a novel technique is provided for conductively interconnecting electrical components in an implantable device or the like. In this regard, the invention is particularly designed to facilitate electrical interconnection of pacemaker lead conductors with connector blocks and electrode terminals.

BACKGROUND OF THE INVENTION

Implantable stimulation devices of the type having electrical circuit components are well known in the medical arts. In one particularly common form, the implantable device comprises a pacemaker unit having an appropriate electrical power supply and related control circuitry for use in electrically stimulating a patient muscle, such as the heart. Such pacemaker units commonly include an hermetically sealed case or housing within which the power supply and control circuitry are protectively encased, in combination with one or more conductive pacemaker leads extending from the housing to the selected muscle structure within the patient. Feedthrough terminals on the pacemaker housing accommodate hermetically sealed passage of electrical conductors to the housing exterior for appropriate connection to the pacemaker lead or leads, typically through the use of so-called connector blocks having set screws or the like for secure lead attachment. The connector blocks and associated feedthrough conductors disposed externally of the pacemaker housing are commonly encased within a sealed head structure, such as an insulative head of cast epoxy or the like.

The commonly used form of welding which has heretofore been satisfactory for making connections in implantable stimulation devices between leads and either electrodes and connectors has been resistance welding which unfortunately is operator dependent with many variables including electrode wear, force, and voltage. The inventors and others have come to recognize that laser welding would be desirable for joining small diameter wire to electrodes and connectors, notwithstanding the fact that resistance welders are less expensive than laser welders.

In many instances, present laser weld design concepts for joining small diameter wire or rod or coiled wire to electrodes and connectors cannot be used to reliably produce a joint. Components made from dissimilar materials having different melting temperatures, normal component fabrication variability, insignificant thermo mass inherent with certain components, imprecise component alignment during assembly, and unlike materials with distinctly different melting temperatures, are major factors that affect the reliability and repeatability of weld connections using conventional design concepts.

Typical of more recent developments in this regard is U.S. Pat. No. 5,458,629, to Baudino et al. In this instance, a ring electrode may be introduced onto an insulated lead so as to form an isodiametric lead construction. The outer layer of insulation forming the lead body is etched or notched, for example, by being laser etched or physically milled to provide a recess in the lead insulation having a depth corresponding to the thickness of the ring electrode intended to be provided at that location. A ring electrode is introduced onto the notched section on the lead in the form of a C-shaped sleeve adaptable to be introduced onto the notched portion of the lead and subsequently formable into a cylindrical shape when closed into position in the notched portion of the lead so that the edges of the C-shaped sleeve are brought to an abutting as opposed to overlapping relationship. A single conductor is brought through the insulation and aligned with a hole in the C-shaped sleeve to be welded to the sleeve, for example, by laser welding. The final affixation procedure involves laser welding the abutting surfaces of the sleeve together, thereby securely forming a ring electrode isodiametrically within the notch on the electrode.

SUMMARY OF THE INVENTION

It was in light of the prior art as just related that the present invention was conceived and has now been reduced to practice. According to the invention, a method is presented of welding an electrically conductive termination component having first and second opposed surfaces to an electrically conductive elongate member extending to a terminal end. The method comprises the steps of forming a substantially circular aperture through the termination component and defined by a rim having a diameter substantially equivalent to the transverse dimension of the elongate member. The terminal end of the elongate member is positioned proximate the termination component overlying the rim of the aperture such that the longitudinal axis of the elongate member is generally coplanar with the center of the aperture. Then, a laser beam is directed transversely of the termination component through the aperture therein toward and onto the elongate member to simultaneously melt the elongate member and the termination component in the region of the aperture and create a mixture of the molten material of both the elongate member and the termination component within the aperture. Upon the cessation of operation of the laser beam, the mixture of the molten material solidifies within the aperture and between the termination component and the elongate member to thereby achieve a welded connection between the elongate member and the termination component. In a preferred embodiment, a ball member is formed at an end of the elongate member and the rim of the aperture in the termination component has a diameter smaller than that of the ball member and the ball member is positioned in engagement with the rim of the aperture.

More specifically, the concept of the invention utilizes a weld design where elongate material, either regular wire or coiled wire or rod, is joined to a larger "termination component" by means of a laser welded "ball-and-socket" joint. The elongate material is fabricated with a spherical end to increase the thermo-mass and laser target assembly. The "termination component" (i.e. electrode or connector) is fabricated with a "target" construction hole somewhat smaller than the diameter of the "ball". The "target" hole is located where the joint will be made. Assembly is accomplished by locating the "ball" in the "target hole" forming a "ball-and-socket" assembly. The assembly is completed by directing the laser through the opposite side of the target hole, directly at the top of the "ball". The laser energy melts and fuses the "ball" and material surrounding the "target hole". A capillary effect draws the molten material into the hole resulting in a concave weld fillet.

Accordingly, a primary object of the present invention is to provide a technique for reliably welding small diameter coiled wire or rod to electrodes and connectors.

Another object of the invention is to provide such a novel welding technique which comprises the steps of forming a ball member at an end of an elongate member, then forming in the termination component an aperture defined by a rim having a diameter smaller than the diameter member, then positioning the ball member in engagement with the rim, then directing a laser beam transversely of the termination component through the aperture and onto the ball member to simultaneously melt the ball member and the termination component in the region of the aperture and create a mixture of the molten material of both the ball member and the termination component within the aperture, then discontinuing operation of the laser beam to allow solidification of the molten material within the aperture to thereby achieve a reliable welded connection between the ball member and the termination component.

A further object of the invention is to provide such a novel welding technique which is performed by a pulse laser.

Yet another object of the invention is to provide such a novel welding technique which includes the step of joining to an end of the elongate member distant from the ball member a proximal end of a wound conductor extending to a remote distal end so that electrical continuity is achieved between the elongate member and the wound conductor.

Still a further object of the invention is to provide such a novel welding technique which includes the step of forming the aperture large enough to firmly support the ball member in engagement with the rim yet small enough to allow the laser beam to pass therethrough and melt the rim of the aperture and the ball member simultaneously.

Other and further features and advantages of the present invention will become more apparent from the following detailed description, taken in conjunction with the accompanying drawings which illustrate, by way of example, the principles of the invention. Throughout the specification, like numerals refer to like parts.

DETAILED DESCRIPTION OF THE PREFERRED EMBODIMENTS

Figure 1:
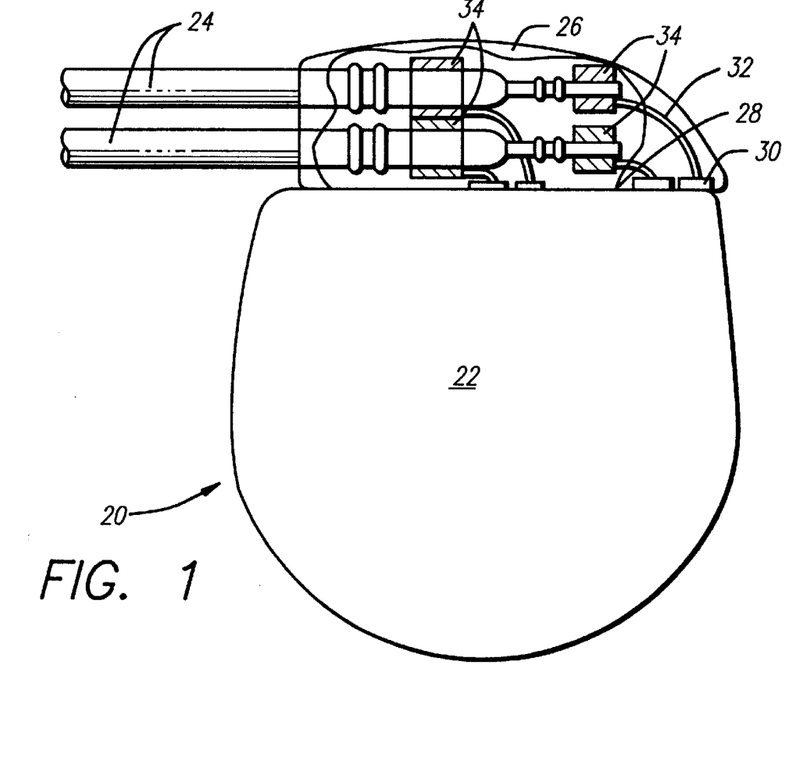
FIG. 1 is a side elevation view of a heart pacemaker unit which is part of a system embodying the technique of the present invention.

Turn now to the drawings and, initially, to FIG. 1 which illustrates an implantable medical device such as a heart pacemaker unit 20. In this regard, heart pacemaker units are generally known in the art for use in electrical stimulation of the heart muscle to regulate patient heartbeat in a controlled manner. The pacemaker unit 20 normally includes an appropriate power source and related electronic circuitry encased within a compact, hermetically sealed, housing or case 22 adapted for implantation directly into the body of a patient at a selected convenient location. In typical fashion, the unit 20 produces a timed sequence of pacing pulses which are coupled to one or more conductive pacemaker leads 24 with the illustrative drawings depicting the pacemaker unit 20 to include a pair of pacemaker leads 20 for so-called duplex mode operation. The pacemaker leads 24 extend from the unit housing 22 for implantation of their distal ends (not presently shown) into target muscle tissue to be stimulated.

As seen in FIG. 1, the pacemaker unit 20 includes a head 26 on the unit housing 22, wherein the head 26 includes means for electromechanically anchoring the pacemaker leads 24 in conductive relation with the pacing signals generated by the circuitry components within the housing 22. More specifically, the pacemaker housing 22 defines a relatively flat mounting platform 28 at one edge thereof. One or more so-called feedthrough terminals 30 project upwardly from this platform and provide hermetically sealed structures of a type known in the art for passing electrical conductors 32 from the interior of the housing 22. These feedthrough terminal conductors 30 are respectively connected by means of the connection technique of the invention to a corresponding set of connector blocks 34 adapted for electromechanical connection to the pacemaker leads 24. Subsequent to electrical interconnection of the feedthrough terminal conductors 32 with the connector blocks 34, these components are encapsulated within a block of insulative epoxy material, or the like, which is cast in place to define the head 26 maintaining the various components in the desired electrically isolated and predetermined interspatial relation.

Figure 2:
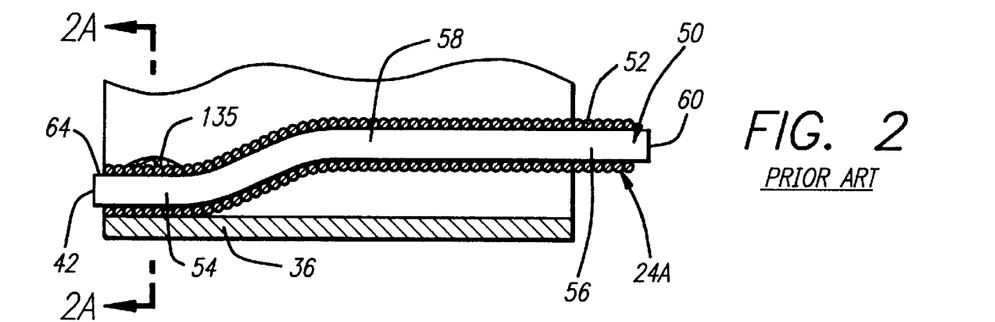
FIG. 2 is a detail side elevation view, in section, illustrating a prior art technique.
Figure 2A:
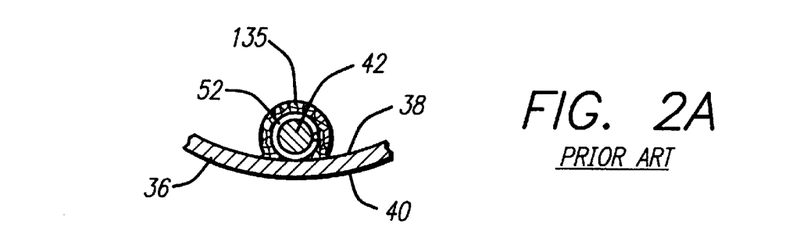
FIG. 2A is a detail cross-section view taken generally along line 2A—2A in FIG. 2.

Turn now to FIGS. 2, 2A, and 2B for an explanation of a known technique for electrically joining leads to a termination component as it has been performed at a distal end of the leads extending from the pacemaker unit 20. As seen in these figures, an electrically conductive termination component 36, typically a ring electrode having first and second opposed surfaces 38, 40, respectively, is to be welded to an electrically conductive elongate member in the form of a pacemaker lead 24A extending to a terminal end 42.

With particular reference to FIG. 2B, at a distal end, the lead 24A is seen to include a rod member 50 and a coil conductor 52 having an inner diameter sufficiently similar to the outer diameter of the rod member as to be fittingly slidable onto the rod member. The rod member 50 is bent so as to have first and second legs 54, 56, respectively, having substantially parallel spaced longitudinal axes and an integral transverse connector member 58 extending between the first and second legs. The coil conductor 52 is slid longitudinally onto the rod member 50 over a distal end 60 and toward the proximal end 42 until a tip end 64 of the coil conductor is substantially adjacent the proximal end 42 of the rod member. Thereupon, it has been customary to create a weld 135 using induction welding techniques.

Figures 3, 3A:
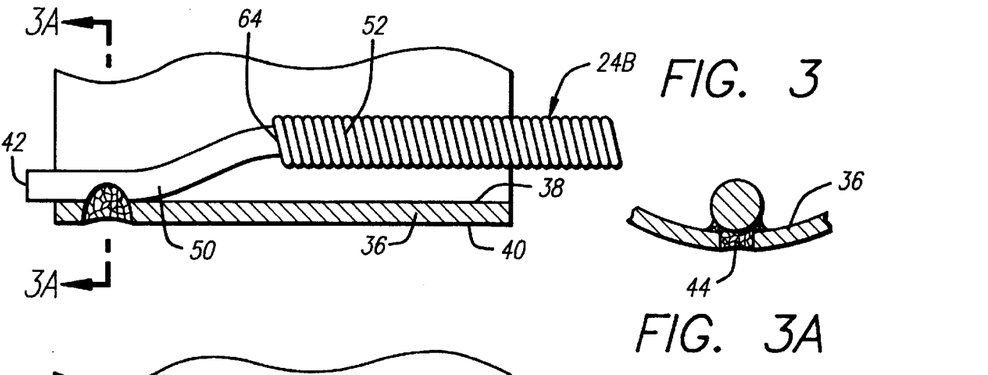
FIG. 3 is a detail side elevation view, in section, illustrating one embodiment of the technique of the present invention.
FIG. 3A is a detail cross-section view taken generally along line 3A—3A in FIG. 3.
Figure 3B:
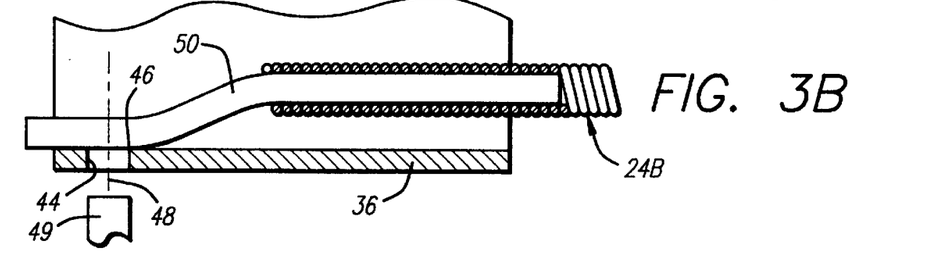
FIG. 3B is a detail side elevation view, in section, illustrating use of a laser for welding.

Turn now to FIGS. 3, 3A, and 3B for an explanation of a novel technique according to the invention for electrically joining leads to a termination component performed at a distal end of the leads extending from the pacemaker unit 20. As seen in these figures, according to the invention, a substantially circular aperture 44 is formed in the termination component so as to extend completely through between the first and second surfaces 38, 40 and is defined by a rim 46 having a diameter substantially equivalent to the transverse dimension of the lead 24B. The terminal end 42 of the lead 24A is positioned proximate the termination component 36 and overlies the rim 46 such that a longitudinal axis of the lead 24A is generally coplanar with the center of the aperture 44.

Thereupon, a laser beam 48, which is preferably from a pulse laser 49, is directed transversely of the termination component 36 through the aperture 44 therein in a direction extending from the surface 40 toward the surface 38 and onto the lead 24A to simultaneously melt the lead and the termination component in the region of the aperture. The energy of a pulsed laser can be adjusted to profile the laser heat over time. Adjusting the heat is beneficial in optimizing the metal interface within the weld. This serves to create a mix of the molten material of both the elongate member and the termination component within the aperture. Upon the cessation of operation of the laser beam 48, the mix of the molten material is thereby allowed to solidify within the aperture and between the termination component and the elongate member. By so doing, a sound welded connection is achieved between the lead 24B and the termination component 36.

In the embodiment of FIGS. 3A and 3B, a pacemaker lead 24B is similar in construction to the lead 24A. However, in the instance of the lead 24B, the tip end 64 of the coil conductor 52 is slid onto the rod member 50 only up to the location of the transverse connector member 58 such that the resulting welded joint is only between the leg 54 of the rod member 50 and the termination component 36.

Figures 4, 4A, 5, 5A:
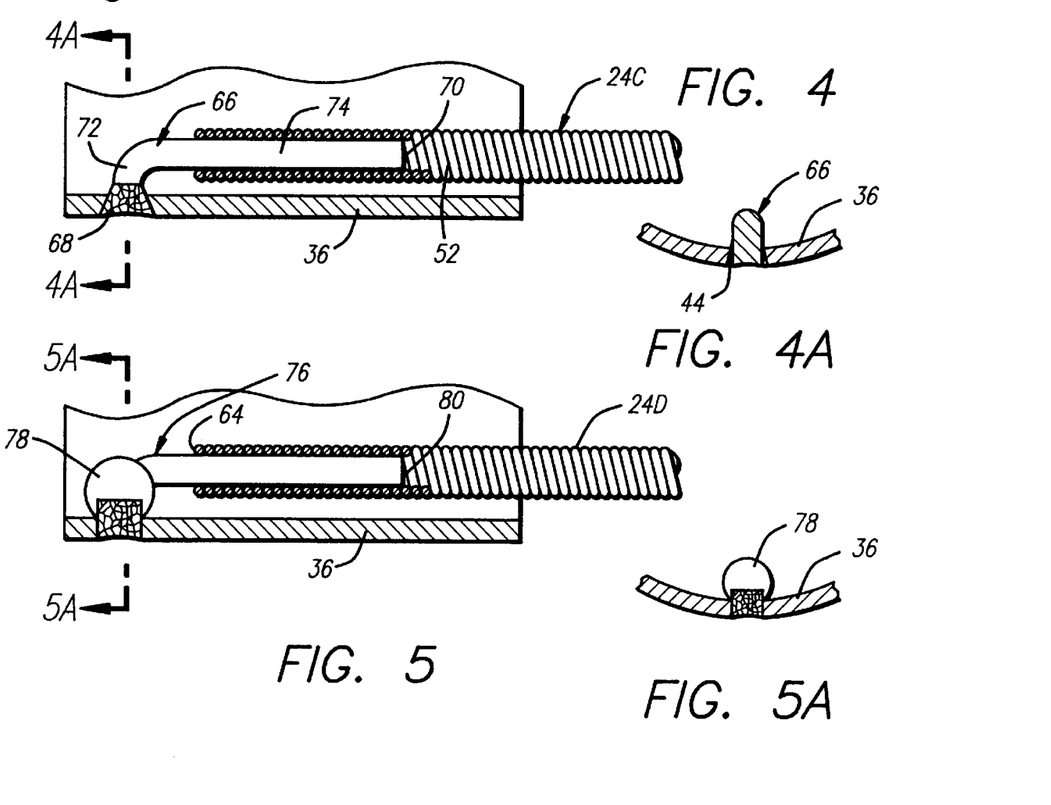
FIG. 4 is a detail side elevation view, in section, illustrating another embodiment of the technique of the present invention.
FIG. 4A is a detail cross section view taken generally along line 4A—4A in FIG. 4.
FIG. 5 is a detail side elevation view, in section, illustrating still another embodiment of the technique of the present invention.
FIG. 5A is a detail cross-section view taken generally along line 5A—5A in FIG. 5.

Another embodiment of the invention is illustrated in FIGS. 4 and 4A. In this instance, a lead 24C includes a rod member 66 which extends between first and second terminal ends, 68, 70, respectively. The terminal end 68 has an outer diameter smaller than the diameter of the aperture 44 in the termination component 36. As in the earlier-described embodiments, the coil conductor 52 has an inner diameter substantially similar to the outer diameter of the rod member 66 but such that the coil conductor is fittingly slidable onto the rod member. In this instance, however, the rod member 66 is bent so as to have first and second legs, 72, 74, respectively, having mutually transverse longitudinal axes. The coil conductor 52 is slid longitudinally onto the second leg 74 of the rod member over the second terminal end 70 until the tip end 64 of the coil conductor is spaced from the first leg 72. Thereupon, the first terminal end 68 of the rod member 66 is inserted into the aperture 44 in the termination component 36 such that the longitudinal axis of the first leg 72 is substantially aligned with the center of the aperture. The earlier described laser welding operation is then performed.

Still another embodiment of the invention is illustrated in FIGS. 5 and 5A. In this instance, a lead 24D includes a rod member 76 which extends between a ball member 78 at a first terminal end extending transversely of the longitudinal axis of the rod member and a second terminal end 80. The ball member 78 has a diameter greater than the diameter of the aperture 44 in the termination component 36. As in the earlier-described embodiments, the coil conductor 52 has an inner diameter substantially similar to the outer diameter of the rod member 76 but such that the coil conductor is fittingly slidable onto the rod member 50. In this instance, the coil conductor 52 is slid longitudinally onto the rod member 76 until the tip end 64 of the coil conductor is spaced from the ball member 78. Thereupon, the ball member 78 is inserted into the aperture 44 in the termination component 36 such that its outer peripheral surface fully engages the rim 46 and the earlier described laser welding operation is then performed.

Figure 6:
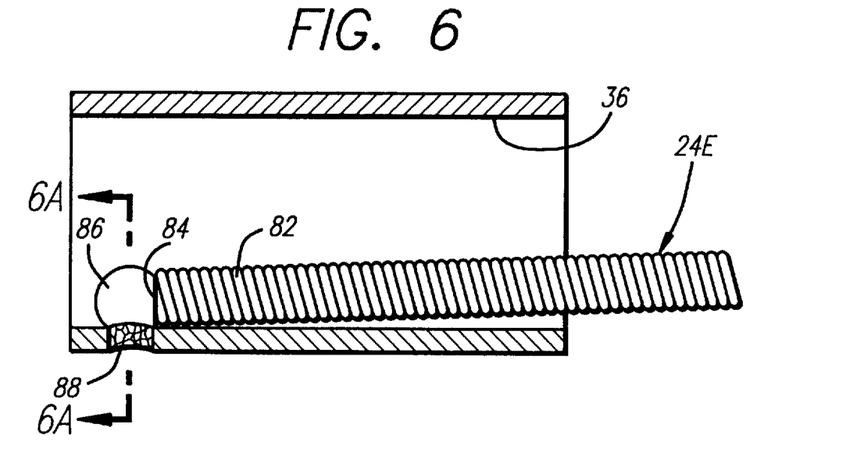
FIG. 6 is a detail side elevation view, in section, illustrating still another embodiment of the technique of the present invention.
Figure 6A:
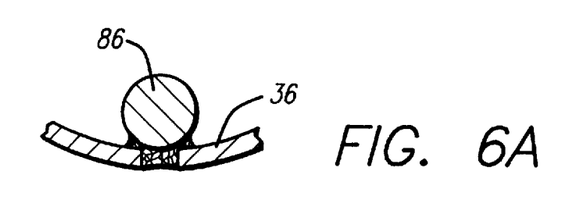
FIG. 6A is a detail cross-section view taken generally along line 6A—6A in FIG. 6.

Yet another, indeed preferred, embodiment of the invention is illustrated in FIGS. 6 and 6A. In this instance, a lead 24E includes a coil conductor 82 having a tip end 84 and a ball member 86 affixed to the tip end and having a diameter greater than the diameter of the aperture 44 in the termination component 36. The center of the ball member is substantially aligned with the longitudinal axis of the coil conductor 82. Thereupon, the ball member 86 is inserted into the aperture 44 in the termination component 36 such that its outer peripheral surface fully engages the rim 46 and the earlier described laser welding operation is then performed.

According to this preferred embodiment of the invention, the ball member 86 is positioned in engagement with the rim 46 of the termination component 36 such that the aperture 44 is generally coextensive with the ball member. With this construction, the beam 48 from the laser 49 directed transversely of the termination component through the aperture 44 impinges on the ball member 84. This operation causes a simultaneously melting of the termination component and of the ball member in the region of the aperture and creates a mixture of the material of the ball member with the material of the termination component in the region of the aperture. It will be appreciated that the aperture 44 is sufficiently large to firmly support the ball member 86 in engagement with the rim 46 and simultaneously to allow the laser beam 48 to pass through the aperture yet small enough to allow the simultaneous melt of the rim 46 of the aperture and of the ball member 86. When this mixture becomes solidified, it achieves a sound welded connection between the ball member and the termination component and forms a concave weld fillet 88 overlying the former aperture.

It will be appreciated that the various embodiments just described with respect to FIGS. 3–6 could be utilized in any environment in which a termination is to be made at either end or anywhere along an electrical lead. While the termination component 36 has been generally illustrated as being cylindrical, in actual fact, it may be flat or of any other number of shapes without altering the concept of the invention. However, some more specific examples will now be presented with respect to the possible use of such connections in the instance of implantable devices such as pacemakers.

Figure 7:
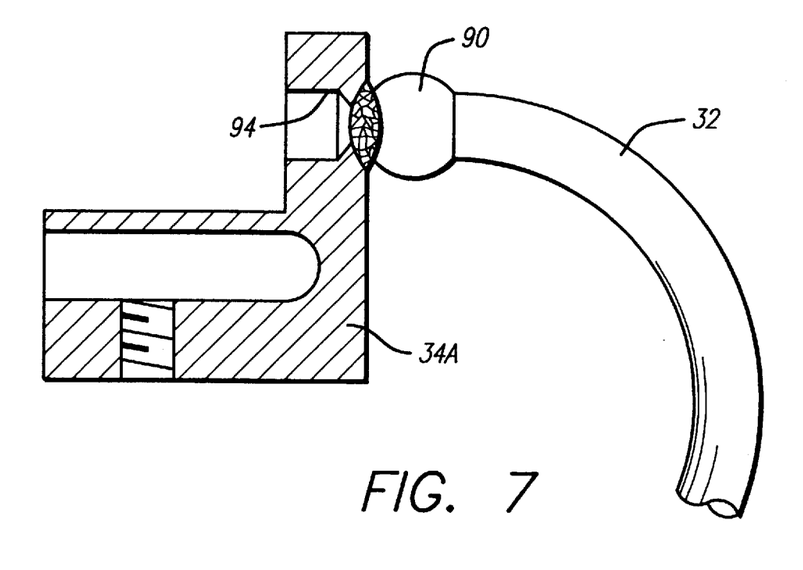
FIG. 7 is a detail side elevation view, partly in section, of components illustrated in FIG. 1.

In FIG. 7, for example, the connection between the electrical conductors 32 and their associated connector blocks 34 at the pacemaker unit 20 (FIG. 1) is made using the technique of the invention. Specifically, a ball member 90 integral with a tip end 92 of the electrical conductor 32 is centered on a longitudinal axis of the conductor and fully engaged with a rim of a through hole 94 in the connector block 34A. Being so positioned, the ball member 90 is then laser welded to the connector block 34A so as to achieve a sound joint as earlier described. It is noteworthy that at the pacemaker unit 20, all conductors and their connections are preferably rigid. The benefits thereby achieved include lower electrical resistance, less expense and, indeed, there is no need to provide for flexure.

Figure 8:
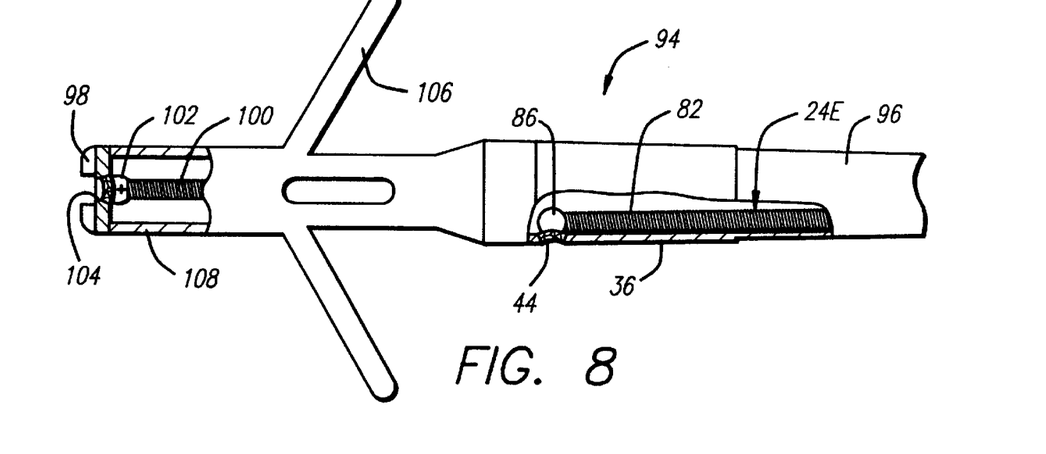
FIG. 8 is a detail top plan view, certain parts being cut away and shown in section, of another part of a system including the heart pacemaker unit of FIG. 1 and utilizing the techniques of the invention.

Turning now to FIG. 8, a distal end 94 of one of the pacemaker leads 24E is illustrated which is at a location distant from the pacemaker unit 20. In this instance, a lead body 96 contains the termination component 36 in the form of a ring electrode and the coil conductor 82 whose ball member 86 is joined thereto in the manner previously described. The configuration of the distal end 98 is that of a bipolar pacing lead of which the termination component 36 is an anode although the concept of the invention is also applicable to unipolar configurations. In this configuration, a tip electrode 98 at an extreme distal end of the lead body 96 is a cathode. A coil conductor 100, also extending from the pacemaker unit 20, terminates at an integral ball member 102 of a construction already described and joined to the tip electrode 98 at a hole 104 therein in a manner as already described. Tines 106 of flexible rubber, or the like, integral with a foremost shaft 108 of the lead body 96 are swept back and serve to secure the lead body 96 and primarily the top electrode 98 to the heart of the person for whom the pacemaker unit 20 is intended.

Figure 8A:
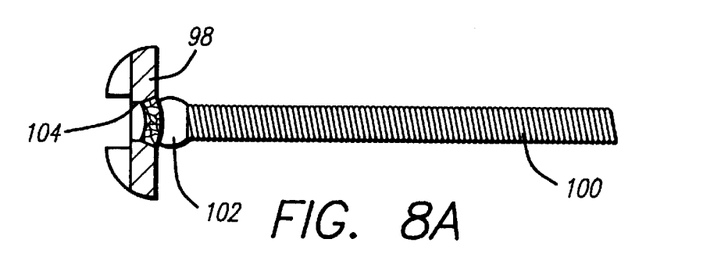
FIG. 8A is an enlarged detail cross-section view of components illustrated in FIG. 8.
Figure 8B:
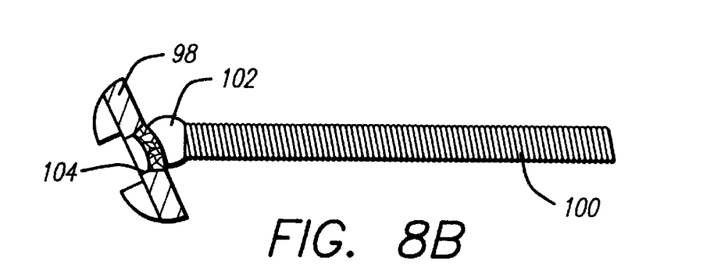
FIG. 8B is an enlarged detail cross-section view, similar to FIG. 8A, illustrating another embodiment thereof.
Figure 8C:
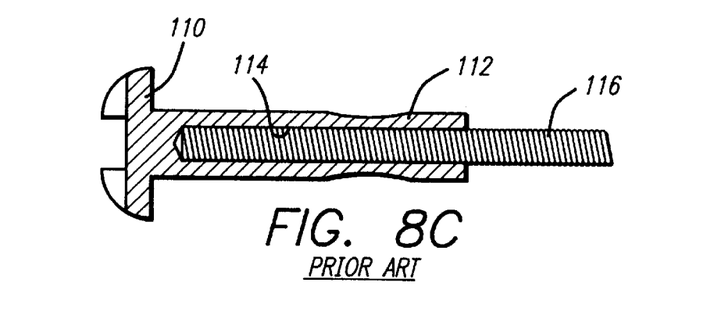
FIG. 8C is an enlarged detail cross-section view, similar to FIG. 8A, illustrating a typical prior art construction.
Figures 9, 9A, 9B, 9C, 9D:
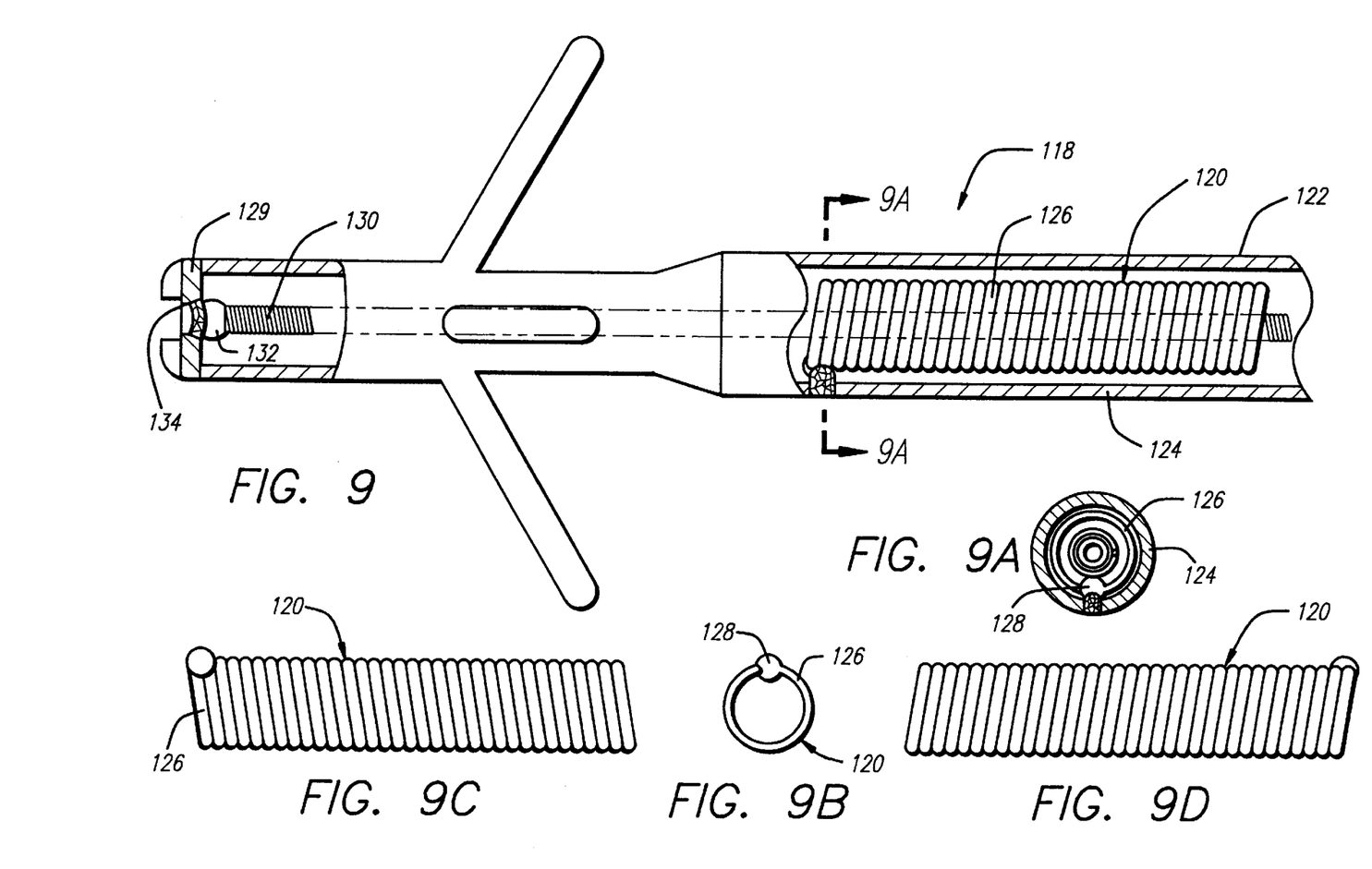
FIG. 9 is a detail top plan view, certain parts being cut away and shown in section, of another embodiment of another part of a system including the heart pacemaker unit of FIG. 1 and utilizing the techniques of the invention.
FIG. 9A is a cross-section view taken generally along line 9A—9A in FIG. 9.
FIG. 9B is a front elevation view of a component illustrated in FIG. 9.
FIG. 9C is a side elevation view, taken from one side, of the component illustrated in FIG. 9B.
FIG. 9D is a side elevation view, taken from the other side, of the component illustrated in FIG. 9B.

The tip electrode 98 is intended to be embedded against heart tissue and it is desirable and even necessary for proper results that the entire face of the tip electrode be so embedded. The flexibility offered by the coil conductor lo aids greatly in achieving this result. For yet more improved results, it may be desired in some applications to so join the ball 102 to the tip electrode 98 that instead of the shaft 100 assuming a perpendicular relationship with the tip electrode (FIG. 8A), it assumes an angular relationship (FIG. 8B). In any event, the constructions illustrated in FIGS. 8A and 8B are significant advances over a typical known construction illustrated in FIG. 8C. In this latter figure, a tip electrode 110 has an integral shank 112 with a longitudinally extending internal bore 114 for the fitting reception of the distal end of a coiled conductor 116. Because of the undue length of the bore 114 and shank 112 the substantially rigid connection thereby resulting between the coiled conductor 116 and the tip electrode 110 largely prevents full-face embedment of the tip electrode against heart tissue.

Still a further embodiment of the invention is illustrated in FIGS. 9, 9A, 9B, 9C, and 9D. In this instance, a distal end 118 of a further modified pacemaker lead 120 is illustrated which is at a location distant from the pacemaker unit 20. In this instance, a lead body 122 contains a termination component 124 in the form of a ring electrode and a coil conductor 126 whose ball member 128 is integral with the extreme end of the wire forming the coil conductor but not joined to the entire projected face of the coil conductor as in previous embodiments. As in the FIG. 8 embodiment, the configuration of the distal end 118 is that of a bipolar pacing lead of which the termination component 124 is an anode. In this configuration, a tip electrode 129 at an extreme distal end of the lead body 122 is a cathode. A coil conductor 130, also extending from the pacemaker unit 20, terminates at an integral ball member 132 of a construction already described and joined to the tip electrode 128 at a hole 134 therein in a manner as already described. The remainder of the construction of the distal end 118 is as previously described with respect to the FIG. 8 embodiment.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A method of welding an electrically conductive elongate member to an electrically conductive termination component comprising the steps of:
   (a) forming a ball member at an end of the elongate member;
   (b) forming in the termination component an aperture defined by a rim having a diameter smaller than the diameter of the ball member;
   (c) positioning the ball member in engagement with the rim of the aperture in the termination component;
   (d) directing a laser beam transversely of the termination component through the aperture therein and onto the ball member to simultaneously melt the ball member and the termination component in the region of the aperture and create a mixture of the molten material of both the ball member and the termination component within the aperture; and
   (e) discontinuing operation of the laser beam to allow solidification of the mixture of the molten material of step (d) within the aperture to thereby achieve a welded connection between the ball member and the termination component.

2. A method, as set forth in claim 1, wherein step (d) is performed by a pulse laser.

3. A method, as set forth in claim 1, including the step of:
   (f) joining to an end of the elongate member distant from the ball member a proximal end of a wound conductor extending to a remote distal end so that electrical continuity is achieved between the elongate member and the wound conductor.

4. A method, as set forth in claim 1, wherein step (b) includes the step of:
   (f) forming the aperture large enough to firmly support the ball member in engagement with the rim and to allow the laser beam to pass therethrough yet small enough to allow the melt of the rim of the aperture and the ball member simultaneously.

5. A method of welding an electrically conductive elongate member comprised of a first material to an electrically conductive termination component comprised of a second material, said method comprising the steps of:
   (a) forming an electrically conductive elongate member into an L-shape having first and second legs;

(b) forming a ball member at an end of the first leg;

(c) forming in the termination component an aperture defined by a rim having a diameter smaller than the diameter of the ball member;

(d) positioning the ball member in engagement with the rim of the aperture in the termination component;

(e) directing a laser beam transversely of the termination component through the aperture therein and onto the ball member to simultaneously melt the ball member and the termination component in the region of the aperture and create a mixture of the first material with the second material within the aperture; and (f) discontinuing operation of the laser beam to allow solidification of the mixture of the first material with the second material in the region of the aperture to thereby achieve a welded connection between the ball member and the termination component.

6. A method, as set forth in claim 5, wherein step (d) is performed by a pulse laser.

7. A method, as set forth in claim 5, including the step of:

(f) joining to an end of the elongate member distant from the ball member a proximal end of a coiled conductor extending to a distal end so that electrical continuity is achieved between the elongate member and the coiled conductor.

8. A method, as set forth in claim 5, wherein step (a) includes the step of:

(f) forming the L-shaped rod out of solid material such that the second leg thereof is a major leg and the first leg thereof is a minor leg shorter than the major leg and has a longitudinal axis transverse of the longitudinal axis of the major leg.

9. A method, as set forth in claim 8, wherein the termination component is a cylinder, and wherein step (d) includes the step of:

(f) positioning the major leg within the cylinder such that the longitudinal axis thereof is parallel to a longitudinal axis of the cylinder.

10. A method, as set forth in claim 5, wherein step (c) includes the step of:

(g) forming the aperture large enough to firmly support the ball member in engagement with the rim and to allow the laser beam to pass therethrough yet small enough to allow the melt of the rim of the aperture and the ball member simultaneously.

11. An implantable stimulation device comprising:

an electrically conductive elongate member comprised of a first material and having a ball member at one end thereof; and an electrically conductive termination component comprised of a second material having an aperture therethrough defined by a rim with a diameter smaller than the diameter of said ball member;

wherein said ball member is positioned in engagement with said rim of said termination component such that the aperture therein is generally coextensive with said ball member;

such that a laser beam directed transversely of said termination component through the aperture therein impinges on said ball member to simultaneously melt said termination component and said ball member in the region of the aperture and create a mixture of said material of said ball member with said material of said termination component in the region of the aperture which, when solidified, achieves a welded connection between said ball member and said termination component and forms a concave weld fillet overlying the former aperture.

12. An implantable stimulation device, as set forth in claim 11, wherein said elongate member includes:

an L-shaped solid rod including first and second legs, said first leg having a longitudinal axis transverse of the longitudinal axis of said second leg, said ball member being at an end of said first leg; and a coiled conductor extending between proximal and distal ends and being integrally joined at said proximal end to an end of said second leg of said solid rod.

13. An implantable stimulation device, as set forth in claim 12, wherein said second leg of said L-shaped solid rod is a major leg and said first leg thereof is a minor leg shorter than said major leg and has a longitudinal axis transverse of the longitudinal axis of said major leg.

14. An implantable stimulation device, as set forth in claim 13:

wherein said termination component is a cylinder; and wherein said major leg is positioned within said cylinder such that the longitudinal axis of said major leg is parallel to a longitudinal axis of said cylinder.

15. An implantable stimulation device, as set forth in claim 11, wherein the aperture is sufficiently large to firmly support said ball member in engagement with said rim and to allow the laser beam to pass therethrough yet small enough to allow the melt of said rim of the aperture and said ball member simultaneously.

16. A method of welding an electrically conductive termination component having first and second opposed surfaces to an electrically conductive elongate member extending to a terminal end and having a longitudinal axis and a transverse dimension, the method comprising the steps of:

(a) forming in the termination component a substantially circular aperture extending therethrough between said first and second surfaces and defined by a rim having a center and a diameter substantially equivalent to the transverse dimension of the elongate member;

(b) positioning the terminal end of the elongate member proximate the first member and overlying the rim of the aperture in the termination component such that the longitudinal axis of the elongate member is generally coplanar with the center of the aperture;

(c) directing a laser beam transversely of the termination component through the aperture therein in a direction from the first surface toward the second surface and onto the elongate member to simultaneously melt the elongate member and the termination component in the region of the aperture and create a mixture of the molten material of both the elongate member and the termination component within the aperture; and (d) discontinuing operation of the laser beam to allow solidification of the mixture of the molten material of step (d) within the aperture and between the termination component and the elongate member to thereby achieve a welded connection between the elongate member and the termination component.

17. A method, as set forth in claim 16, including the steps of:

(e) providing the elongate member such that it includes:
a rod member having an outer diameter and first and second terminal ends; and
a coil conductor having a tip end and an inner diameter substantially similar to the outer diameter of the rod member but such that the coil conductor is fittingly slidable onto the rod member;

(f) bending the rod member so as to have first and second legs having substantially parallel spaced longitudinal axes and an integral transverse connector member extending between said first and second legs; and (g) before step (b), sliding the coil conductor longitudinally onto the rod member over the second terminal end and toward the first terminal end until the tip end of the coil conductor is substantially adjacent the transverse connector member.

18. A method, as set forth in claim 16, including the steps of:

(e) providing the elongate member such that it includes:
a rod member having first and second terminal ends, the first terminal end having an outer diameter smaller than the diameter of the aperture in the termination component; and
a coil conductor having a tip end and an inner diameter substantially similar to the outer diameter of the rod member but such that the coil conductor is fittingly slidable onto the rod member; and (f) bending the rod member so as to have first and second legs having mutually transverse longitudinal axes; and (g) before step (b), sliding the coil conductor longitudinally onto the second leg of the rod member over the second terminal end, onto the second leg until the tip end of the coil conductor is spaced from the first leg of the rod member; and wherein step (b) includes the step of:

(h) inserting the first terminal end of the rod member into the aperture in the termination component such that the longitudinal axis of the first leg of the rod member is substantially aligned with the center of the aperture.

19. A method, as set forth in claim 16, including the steps of:

(e) providing the elongate member such that it includes:
a rod member having a longitudinal axis, an outer diameter, and first and second terminal ends and a ball member at the first terminal end and extending transversely of the longitudinal axis thereof, the ball member having a diameter greater than the diameter of the aperture in the termination component; and
a coil conductor having a tip end and an inner diameter similar to the outer diameter of the rod member but such that the coil conductor is fittingly slidable onto the rod member; and (f) before step (b), sliding the coil conductor longitudinally onto the second leg of the rod member over the second terminal end, onto the second leg until the tip end of the coil conductor is spaced from the ball member.

20. A method, as set forth in claim 16, including the steps of:

(e) providing the elongate member such that it includes:
a coil conductor having a tip end; and
a ball member affixed to the tip end of the coil conductor having a diameter greater than the diameter of the aperture in the termination component; and (f) positioning the ball member in engagement with the rim of the aperture in the termination component.

* * * * *